United States Patent
Rourke et al.

(10) Patent No.: US 7,122,059 B2
(45) Date of Patent: *Oct. 17, 2006

(54) SELECTIVELY THINNED COILED-SHEET STENTS AND METHODS FOR MAKING THEM

(75) Inventors: Jonathan M. Rourke, Los Altos, CA (US); Yi Yang, San Francisco, CA (US)

(73) Assignee: Endotex Interventional Systems, Inc., Cupertino, CA (US)

( * ) Notice: Subject to any disclaimer, the term of this patent is extended or adjusted under 35 U.S.C. 154(b) by 548 days.

This patent is subject to a terminal disclaimer.

(21) Appl. No.: 10/354,704

(22) Filed: Jan. 29, 2003

(65) Prior Publication Data

US 2003/0135263 A1  Jul. 17, 2003

Related U.S. Application Data

(63) Continuation of application No. 09/693,334, filed on Oct. 20, 2000, now Pat. No. 6,547,818.

(51) Int. Cl.
  *A61F 2/24* (2006.01)
  *A61F 2/76* (2006.01)
  *A61F 2/06* (2006.01)

(52) U.S. Cl. ..................... 623/901; 623/1.15
(58) Field of Classification Search .......... 623/901, 623/1.11–1.21; 606/108, 198
See application file for complete search history.

(56) References Cited

U.S. PATENT DOCUMENTS

| 5,443,500 | A |   | 8/1995  | Sigwart |           |
|-----------|---|---|---------|---------|-----------|
| 5,637,113 | A | * | 6/1997  | Tartaglia et al. | 623/1.42 |
| 5,681,346 | A |   | 10/1997 | Orth et al. |       |
| 5,807,404 | A |   | 9/1998  | Richter |           |
| 5,824,052 | A | * | 10/1998 | Khosravi et al. | 623/1.15 |
| 5,836,966 | A |   | 11/1998 | St. Germain |       |
| 5,843,117 | A |   | 12/1998 | Alt et al. |       |
| 5,843,175 | A |   | 12/1998 | Frantzen |       |
| 5,913,895 | A |   | 6/1999  | Burpee et al. |   |
| 5,938,697 | A |   | 8/1999  | Killion et al. |  |
| 5,980,553 | A |   | 11/1999 | Gray et al. |    |
| 6,027,526 | A |   | 2/2000  | Limon et al. |   |
| 6,042,606 | A |   | 3/2000  | Frantzen |       |
| 6,156,062 | A | * | 12/2000 | McGuinness | 623/1.22 |
| 6,425,915 | B1| * | 7/2002  | Khosravi et al. | 623/1.22 |

FOREIGN PATENT DOCUMENTS

FR   2 764 794   6/1997

OTHER PUBLICATIONS

PCT Publication No. WO 98/58600, Pierre Hilaire, et al., "Expandable Stent with Variable Thickness", Dec. 30, 1998.

(Continued)

*Primary Examiner*—Vy Bui
(74) *Attorney, Agent, or Firm*—Orrick, Herrington & Sutcliffe LLP

(57) ABSTRACT

A coiled-sheet stent includes a tubular body having a longitudinal axis, a circumference, and a thickness, and having a size configured for introduction into a body lumen. The tubular body includes a plurality of cylindrical bands, each band including a generally zig-zag pattern defined by a series of sequential arcuate-shaped diagonal elements connected to one another and extending about the circumference. Longitudinal connectors extend between adjacent cylindrical bands. Slots are formed in the tubular body oriented about the circumference of the tubular body, thereby providing reduced thickness regions in the longitudinal connectors that have a thickness that is substantially smaller than the thickness of the cylindrical bands of the tubular body.

5 Claims, 2 Drawing Sheets

OTHER PUBLICATIONS

PCT Publication No. WO 00/28921 entitled "Coiled-Sheet Stent-Graft with Exo-Skeleton", May 25, 2000.
PCT Publication No. WO 01/00112 A1 entitled "Variable Thickness Stent and Method of Manufacture Thereof", Jan. 4, 2001.
EP Publication No. 0 951 877 A2 entitled "A Multi-Laminate Stent Having Superelastic Articulated Sections", Oct. 27, 1999.
EP Publication No. 1 042 997 A1 entitled "Stent With Variable Wall Thickness", Oct. 11, 2000.

* cited by examiner

SELECTIVELY THINNED COILED-SHEET STENTS AND METHODS FOR MAKING THEM

RELATED INFORMATION

This application is a continuation of application Ser. No. 09/693,334, now U.S. Pat. No. 6,547,818, the disclosure of which is expressly incorporated herein by reference.

FIELD OF THE INVENTION

The present invention relates generally to prostheses for implantation within body lumens, and more particularly to coiled-sheet stents that include selectively thinned regions, and to methods for making such stents.

BACKGROUND

Tubular prostheses or "stents" are often implanted within blood vessels, for example, within the coronary and carotid arteries, for treating atherosclerotic disease that may involve one or more stenoses. Stents generally have a tubular shape capable of assuming a radially contracted condition to facilitate introduction into a patient's vasculature, and an enlarged condition for engaging the vessel wall at a treatment location. In its contracted condition, the stent may be placed on or in a delivery device, such as a catheter, percutaneously introduced into a patient's vasculature and advanced to a target treatment location, such as a stenosis, occlusion, or other lesion within a blood vessel. Once at the treatment location, the stent may be deployed and expanded to its enlarged condition, thereby engaging the wall of the vessel and substantially anchoring the stent in place.

Plastically deformable tubular stents have been suggested that are initially provided in their contracted condition, and placed over a balloon on a delivery catheter. At the treatment location, the balloon is inflated to plastically deform the stent until it is expanded to its enlarged condition. Thus, the stent may be expanded to any size within a specified range to ensure that the stent substantially engages the wall of the vessel.

Self-expanding tubular stents have also been suggested that are biased to assume their enlarged condition but may be radially compressed to a contracted condition. The stent may be mounted to a delivery device and constrained in a contracted condition during delivery, for example, by an overlying sheath. At the treatment location, the stent may be released, for example, by retracting the overlying sheath, the stent automatically expanding to its enlarged condition to engage the vessel wall.

In addition to tubular stents, coiled-sheet stents have been suggested. A flat sheet is rolled into a spiral shape having overlapping inner and outer longitudinal sections that defines a contracted condition. The coiled-up sheet may be biased to at least partially unroll to assume an enlarged condition, and/or may be unrolled and radially expanded using a balloon. The coiled-sheet stent may have a lattice-like structure and a plurality of fingers or teeth along the inner longitudinal section for engaging openings in the lattice. Once the coiled-sheet stent is expanded at a treatment location, the fingers on the inner longitudinal section may engage corresponding openings in the lattice to lock the stent in the enlarged condition.

Coiled-sheet stents may provide enhanced anchoring within the blood vessel because the size of the fully expanded stent may be more precisely controlled. A conventional rectangular lattice, such as that disclosed in U.S. Pat. No. 5,443,500 issued to Sigwart, however, may result in a coiled-sheet stent that is more rigid transverse to its longitudinal axis than desired, i.e., that may not bend as easily as desired, particularly when being delivered through tortuous anatomy.

Accordingly, it is believed that a stent that provides enhanced flexibility would be considered useful.

SUMMARY OF THE INVENTION

The present invention is directed to prostheses for implantation within body lumens, and more particularly to stents that include selectively thinned regions to enhance the flexibility of the stent, and to methods for making such stents.

In accordance with one aspect of the present invention, a stent is provided that includes a generally tubular body having a longitudinal axis and a circumference, and having a size configured for introduction into a body lumen. A plurality of cylindrical bands are formed in the tubular body, each band including a generally zig-zag pattern. The generally zig-zag pattern may include a series of sequential diagonal elements connected to one another and extending about the circumference, the diagonal elements preferably having a generally arcuate shape. All diagonal elements in each band are preferably oriented in either a clockwise or counter-clockwise direction about the circumference to facilitate packing of the stent.

A plurality of longitudinal connectors are provided extending between and connecting adjacent cylindrical bands, the longitudinal connectors having reduced thickness regions having a thickness $t_1$ in a radial direction that is substantially smaller than a thickness $t_0$ of the adjacent cylindrical bands. In a preferred form, the thickness $t_1$ of the reduced thickness regions is not more than about two thirds the thickness $t_0$ of the cylindrical bands, and more preferably not more than about one half.

In a preferred embodiment, the tubular body is a coiled-sheet, although the principles of the present invention may apply equally well to substantially enclosed tubular stents. The tubular body is generally expandable between a contracted condition for facilitating introduction into a body lumen and an enlarged condition for engaging a wall of a body lumen. Preferably, the tubular body is biased towards the enlarged condition, and may exhibit temperature-activated shape memory properties. The generally zig-zag pattern may be expandable between an unstretched condition and a stretched condition, the zig-zag pattern being biased towards the stretched condition above a transition temperature, which is substantially below body temperature.

In accordance with another aspect of the present invention, a stent is provided that includes a generally tubular body having a longitudinal axis, a circumference, and a thickness $t_0$, and having a size configured for introduction into a body lumen. A plurality of cells are formed in the tubular body, a plurality of connectors extending between and connecting adjacent cells, and a plurality of slots are formed in the tubular body and oriented substantially perpendicular to the longitudinal axis about the circumference of the tubular body, the slots defining a thickness $t_1$ that is substantially less than the thickness $t_0$ of the tubular body.

In accordance with still another aspect of the present invention, a method for fabricating a stent is provided that includes providing a flat sheet including a length, a width, and a thickness $t_0$. A plurality of openings are formed in the sheet to define a multi-cellular structure. A plurality of slots are formed in the sheet, e.g., by cutting into the sheet with a saw, that are aligned substantially perpendicular to the length of the sheet, the slots having a reduced thickness $t_1$ that is less than the thickness $t_0$ of the sheet. Preferably, the sheet is formed from a shape memory alloy, and the plurality of slots are formed in the sheet without substantially changing mechanical properties of the shape memory alloy. The sheet is rolled about its length into a tubular body, the tubular body having a diameter configured for introduction into a body lumen.

In a preferred method, the step of forming a plurality of openings in the sheet includes forming a plurality of cells and longitudinal connectors in the sheet. Longitudinally adjacent cells are preferably connected to one another by the longitudinal connectors, which are aligned in sets substantially perpendicular to the length of the sheet. The plurality of slots are preferably formed such that a slot intersects each set of longitudinal connectors, thereby providing a reduced thickness region in each of the longitudinal connectors. The reduced thickness regions of the connectors may enhance a flexibility characteristic of the resulting stent, e.g., facilitating bending of the stent when it is advanced through tortuous anatomy.

Other objects and features of the present invention will become apparent from consideration of the following description taken in conjunction with the accompanying drawings.

DETAILED DESCRIPTION OF THE PREFERRED EMBODIMENTS

Figure 1A:
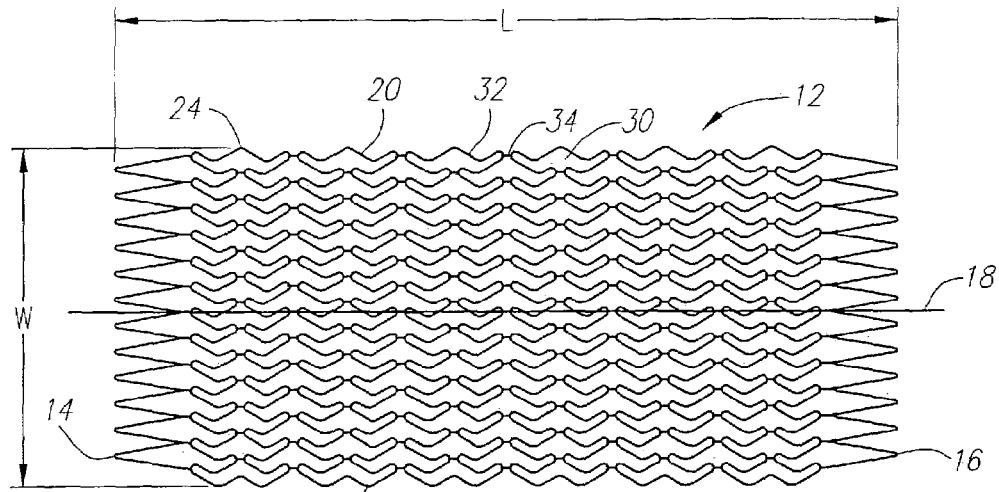
FIGS. 1A and 1B are side views of a flat sheet, in its compressed and expanded states, respectively, for forming a coiled-sheet stent, in accordance with the present invention.

Turning now to the drawings, FIGS. 1A–4 show a preferred embodiment of a coiled-sheet stent 10, in accordance with one aspect of the present invention. As best seen in FIGS. 1A and 1B, the coiled-sheet stent 10 is generally formed from a substantially flat sheet 12 having first and second ends 14, 16 defining a longitudinal axis 18 therebetween. The sheet 12 also includes first and second longitudinal edges 20, 22, the first edge 20 having a plurality of protrusions 24 extending therefrom substantially perpendicular to the longitudinal axis 18. The sheet 12 has an initial thickness $t_0$ (shown in FIG. 3) that may range from between about 0.005–0.009 inch (0.15–0.25 mm), and preferably between about 0.0065–0.0075 inch (0.16–0.19 mm).

In addition, the sheet 12 has a length L and a width W, as shown in FIG. 1A. The length L may be selected to ensure that the stent is sufficiently long to substantially cover a lesion at a treatment location and/or to engage healthy tissue on either side of the lesion. For example, the length L may range from between about 0.75–2.0 inches (20–50 mm), depending upon the specific anatomy to be stented. The width W may be selected to provide a coiled-sheet stent that has a desired diameter in its enlarged condition, i.e., to substantially engage a wall of the blood vessel or other body lumen being treated. The width W is preferably selected such that when the stent assumes its enlarged diameter, e.g., between about 0.075–0.60 inch (1.5–15 mm), inner and outer sections of the coiled-sheet continue to at least partially overlap, as described further below. As the stent mesh is designed to be compressed in the width dimension when stored in the delivery system, the compressed width W of the stent required to address these typical diameters may depend upon the degree of compression that may be achieved with the mesh. Typically, the mesh may be designed to be successfully compressed between 100% and 300% in the width dimension. For example, in the expanded stent condition, the width W may range from between about 1.0–1.5 inches (25–40 mm).

Returning to FIGS. 1A and 1B, the sheet 12 includes a plurality of cells 30 formed therein from substantially diagonal elements 32 and longitudinal connectors 34, thereby defining a multi-cellular mesh structure. The cells 30 are preferably arranged in columns and rows defining a lattice-like structure and providing a plurality of openings for receiving the protrusions 24, as described further below. Preferably, cells 30 within each column are directly connected to one another, while cells 30 in adjacent columns have longitudinal connectors 34 extending between and connecting them.

Within the multi-cellular mesh structure of the sheet 12, end points of adjacent substantially diagonal elements 32 are connected to one another to provide generally zig-zag patterns that extend substantially perpendicularly to the longitudinal axis 18. The substantially diagonal elements 32 are preferably capable of pivoting about these end points, thereby allowing the cells 30 to expand and/or contract in a direction substantially perpendicular to the longitudinal axis 18. Thus, the cells 30 may be capable of assuming a compressed or "unstretched" state, shown in FIG. 1A, and an expanded or "stretched" state, shown in FIG. 1B.

The longitudinal connectors 34 extend between and connect adjacent pairs of zig-zag patterns where the end points of the adjacent substantially diagonal elements 32 connect to one another. Preferably, adjacent cells 30 are out-of-phase with one another, e.g., by ninety degrees, such that the connectors 34 extend between end points of the adjacent cells 30 that are closest to one another. This may minimize the connectors 34 being subjected to longitudinally compressive forces when the stent 10 assumes its expanded diameter that may otherwise cause buckling of the connectors 34.

Figure 2:
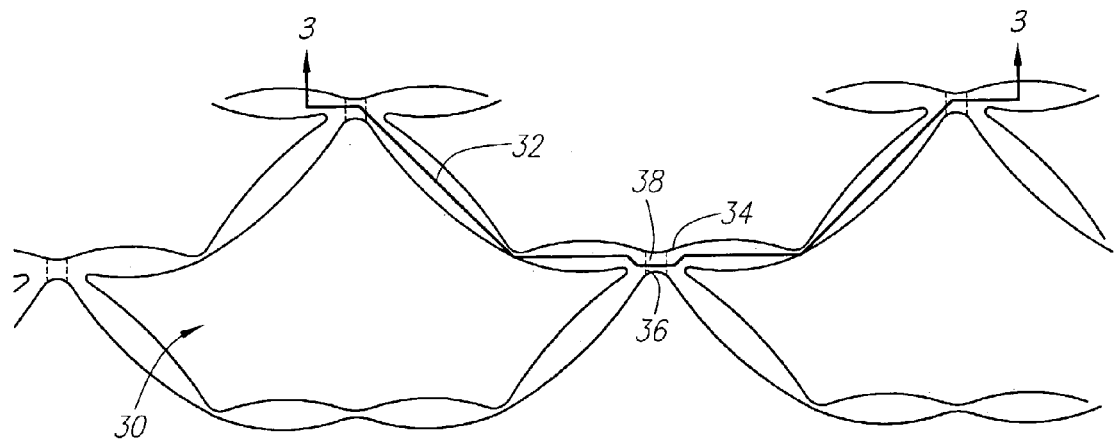
FIG. 2 is a detail of the flat sheet of FIG. 1B, showing a preferred embodiment of a cell structure for the coiled-sheet stent in its expanded state.

The cells provided in a stent in accordance with the present invention may take on a number of different forms. For example, application Ser. No. 09/192,977, filed Nov. 16, 1998, the disclosure of which is expressly incorporated herein by reference, discloses a number of such arrangements. With particular reference to FIG. 2, a preferred embodiment of a multi-cellular mesh structure is shown that includes a plurality of cells 30, including substantially diagonal elements 32 having an arcuate shape. Within each column or cylindrical band, all of the arcuate-shaped diagonal elements 32 are preferably oriented in the same direction, i.e., either in a "clockwise" or "counterclockwise" direction about the circumference. This feature may facilitate "packing" of the diagonal elements 32 with one another, i.e., for compressing the coiled-sheet stent 10 into its unstretched condition without causing overlapping of the diagonal elements. More preferably, all of the diagonal elements 32 in all of the cells of the stent 10 are preferably oriented clockwise, as viewed from FIG. 4. Thus, arcuate portions of underlying diagonal elements 32 may be oriented away from overlying diagonal elements 32, which may facilitate sliding of the inner and outer sections and reduce the risk of underlying diagonal elements catching on overlying diagonal elements during expansion.

Figure 1B:
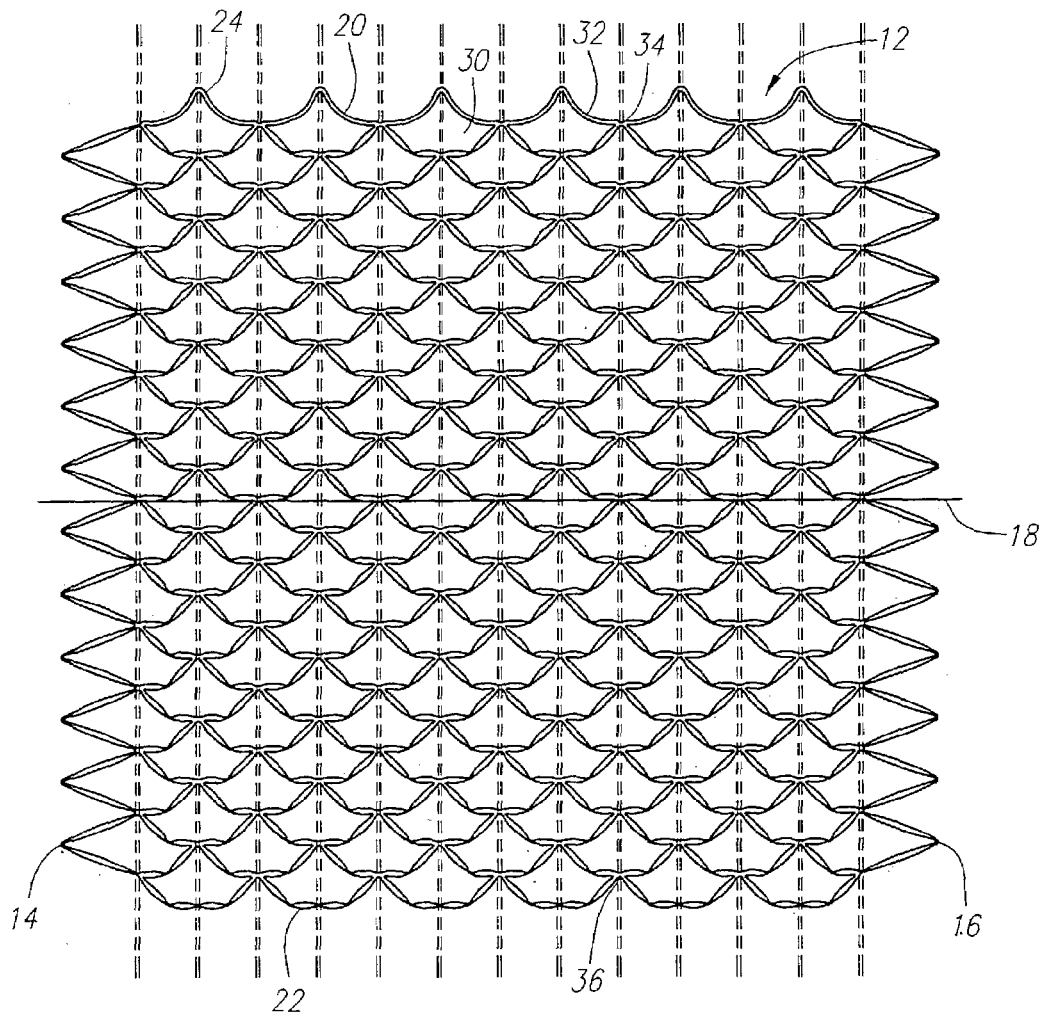
Figure 3:
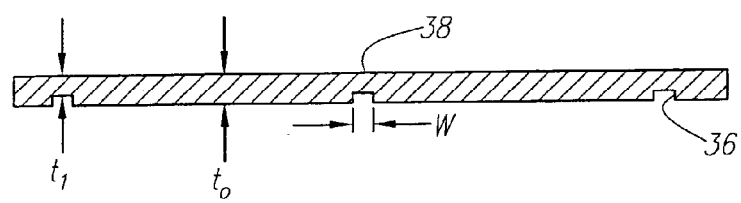
FIG. 3 is a cross-sectional view taken along line 3—3 of FIG. 2.

As best seen in FIGS. 1B, 2, and 3, a plurality of slots 36 are provided in the sheet 12, the slots 36 preferably being oriented substantially perpendicular to the longitudinal axis 18. The slots 36 have a predetermined depth defining a reduced thickness $t_1$ that is substantially less than the initial thickness $t_0$ of the sheet 12. Preferably, the longitudinal connectors 32 are aligned in sets, each set being intersected by a slot 36. Thus, each of the longitudinal connectors 32 preferably includes a reduced thickness region 38 having a width w that extends at least-partially along a length of the longitudinal connectors 32.

Alternatively, instead of discrete slots, the selective thinning may be applied to a wider region and thus create a more distributed compliance. Also, as a design alternative, the depth of thinning may be varied at different points within the stent, for example, at different locations along the length of the stent, so as to create-local regions of greater or lesser flexibility. For example, it may be desirable in some applications to provide for increased flexibility at end regions of the stent and less flexibility in a center region of the stent.

The slots 36 or reduced thickness regions 38 may enhance a flexibility characteristic of the stent 10, facilitating bending of the stent 10 transverse to its longitudinal axis 18, as described further below. The benefit obtained by varying a "thickness" dimension of the diagonal elements or connectors, i.e., the dimension substantially perpendicular to the plane defined by the flat sheet (or radially when the sheet is rolled into its tubular form), may be in addition to any flexibility provided by varying a "width" of the diagonal elements or connectors, i.e., the dimension substantially parallel to the plane defined by the sheet (or longitudinally or circumferentially when the sheet is rolled into its tubular form).

In a preferred embodiment, the thickness $t_1$ at the slots 36 or reduced thickness regions 38 is not more than about two thirds the initial thickness $t_0$ of the sheet 12, and preferably not more than about half the initial thickness $t_0$ of the sheet 12. Thus, for a sheet 12 having a thickness $t_0$ of about 0.0053 inch, the reduced thickness regions 38 preferably have a thickness $t_1$ of about 0.0027 inch or less. In addition, the width w of the slots 36 or reduced thickness regions 38 may be between about 0.002–0.006 inch (0.05–0.15 mm), and preferably between about 0.003–0.005 inch (0.075–0.125 mm). The slots 36 may extend only partially along the length of the connectors 34, as shown, or alternatively may have a width corresponding substantially to the entire length of the connectors 34 (not shown).

Figure 4:
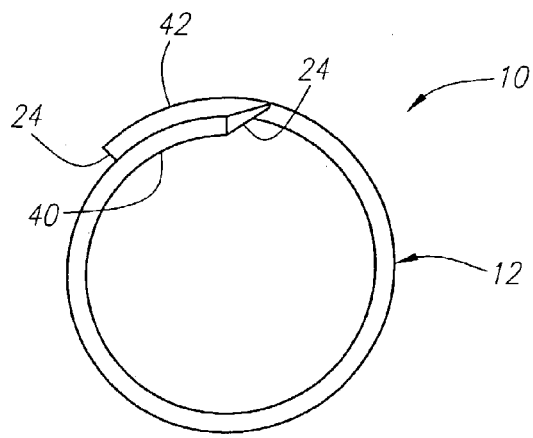
FIG. 4 is an end view of the sheet of FIGS. 1A and 1B rolled into a coiled-sheet stent.

As best seen in FIG. 4, the sheet 12 is preferably provided in a coiled-up condition, defining overlapping inner and outer longitudinal sections 40, 42 that may slide in a circumferential direction with respect to one another to allow radial expansion of the coiled-sheet stent 10 between a contracted condition and one or more enlarged conditions. The coiled-up sheet stent 10 is preferably biased to at least partially unroll to allow radial expansion. Alternatively, the coiled-up sheet stent 10 may be biased to the contracted condition or may be plastically deformable, thereby requiring a balloon or other expandable member to radially expand the stent 10 to its enlarged condition.

Additional information on coiled-sheet stents may be found, for example, in U.S. Pat. No. 4,577,631 issued Mar. 25, 1986 in the name of Kreamer, U.S. Pat. No. 5,007,926 issued Apr. 16, 1991 in the name of Derbyshire, U.S. Pat. No. 5,158,548 issued Oct. 28, 1992 in the name of Lau et al., U.S. Pat. No. Re 34,327 reissued Jul. 27, 1993 in the name of Kreamer, U.S. Pat. No. 5,423,885 issued Jun. 13, 1995 in the name of Williams, U.S. Pat. No. 5,441,515 issued Aug. 15, 1995 in the name of Khosravi et al., U.S. Pat. No. 5,443,500 issued Aug. 22, 1995 in the name of Sigwart, and in co-pending applications Ser. Nos. 09/192,977 filed Nov. 16, 1998, 09/427,260 filed Oct. 25, 1999, and 09/347,845 filed Jul. 2, 1999. The disclosures of these references and any others cited therein are expressly incorporated herein by reference.

In a preferred embodiment, the stent 10 is formed from a shape memory alloy, such as an alloy of nickel and titanium ("Nitinol"), exhibiting temperature-activated shape memory properties at or below body temperature. For example, at a first temperature (e.g., a temperature at which the Nitinol alloy is in its martensitic phase), the cells 30 may be biased to assume the circumferentially compressed or unstretched state, such as that shown in FIG. 1A. At a higher second temperature (e.g., above a transition temperature wherein the Nitinol alloy may undergo austenitic transformation to its austenitic phase), the cells 30 may become biased to assume the circumferentially expanded or stretched state, such as that shown in FIG. 1B. Preferably, the first temperature is generally at or below ambient temperature, such as about 25 degrees Celsius or less, and the second temperature is generally between ambient temperature and body temperature, i.e., at or below body temperature, such as about 37 degrees Celsius or less.

When the stent 10 is biased to the expanded state of FIG. 1B, e.g., at the second temperature, the longitudinal connectors 34 are preferably biased to extend substantially axially parallel to the longitudinal axis 18 of the stent 10. Because of the slots 36, the longitudinal connectors 34 may deflect to accommodate bending of the stent 10 substantially transversely to its longitudinal axis 18. Upon deployment, however, the longitudinal connectors 34 are biased to return to their substantially axial orientation to facilitate scaffolding of a vessel, as described below.

To manufacture a stent 10 in accordance with the present invention, a relatively thin, substantially flat sheet 12 is provided formed from a biocompatible material, such as a metal or polymer, and preferably from a Nitinol alloy or other material capable of exhibiting thermally-activated shape memory properties. The slots 36 are formed in the sheet 12, preferably by removing material from the sheet 12 using a variety of known methods. In a preferred method, a wafer saw (not shown) is used, preferably having a blade with a super low grit abrasive thereon. The sheet 12 is placed in a water bath, and the blade of the wafer saw is directed across the width of the sheet 12 within the water, thereby creating a series of substantially uniform depth slots in the sheet 12. Due to the immersion in water (or alternatively other cooling liquid), the sheet 12 may be maintained at a substantially uniform, relatively low temperature, preferably below 150 degrees Fahrenheit, during the cutting of the slots. Thus, the slots 36 may be formed without substantially changing the mechanical properties of the sheet material, which may be particularly important to maintain the shape-memory aspects of the resulting stent 10. Alternatively, a photoresist/chemical etching process, may be used, a laser may be used, or a scribe, e.g., having a diamond tip, may be used to form the slots 36 in the sheet 12.

The cells 30, the protrusions 24, and/or any other openings for the multi-cellular structure may then be formed in the sheet 12 using a number of conventional processes, such as laser cutting, die and punch, or chemical etching. Alternatively, the multi-cellular structure may be formed in the sheet 12 before forming the slots 36 therein.

In a preferred method, the cells 30 are initially formed in their stretched state (FIG. 1B), and the sheet 12 is subsequently heat treated. For example, for a Nitinol alloy, the stretched state of the cells 30 may be set when the Nitinol alloy is in its austenitic phase, i.e., undergoing heat treatment at a temperature of about 500 degrees Celsius or higher, to activate the shape memory of the material. After the sheet 12 has cooled, i.e., such that the stent material undergoes martensitic transformation to its martensitic phase, e.g., at a temperature at or below ambient temperature, the cells 30 are compressed, i.e., plastically deformed, into their unstretched state (FIG. 1A).

The sheet 12 is then rolled to provide a coiled-sheet stent 10, having overlapping inner and outer longitudinal sections 40, 42, as shown in FIG. 4. Preferably, the coiled-sheet stent 10 is constrained in a relatively tightly rolled, or "contracted" condition for facilitating introduction into a patient, as described further below. In alternative embodiments, the sheet 12 may be rolled and then the edges attached to one another, e.g., using sonic welding or other bonding methods, to provide an enclosed tubular stent.

Once the stent is in its contracted condition, it may be mounted on or in a delivery device (not shown) in preparation for implantation within a body lumen of a patient. The delivery device preferably has a size adapted for percutaneous introduction into a body lumen of a patient, preferably within their vasculature. For example, the stent may be placed within a sheath with a slidable bumper within the sheath adjacent the stent (not shown). Alternatively, the stent may be mounted on a catheter with a retractable sheath overlying the stent and catheter (not shown). In further alternatives, other mechanisms may be provided for constraining the stent in its contracted condition and/or securing it to a delivery device, such as a wire or thread (not shown) which may be woven through overlapping layers of the stent to prevent premature unrolling.

In a preferred method of implantation, the distal end of a catheter-sheath assembly with the stent therein may be percutaneously introduced into a patient's vasculature, and advanced to a target treatment location, such as a stenosis within the coronary, carotid, cerebral, renal arteries, and the like. As the stent reaches body temperature within the patient, the transition temperature of the stent material is surpassed (e.g., for Nitinol material, such that the material undergoes austenitic transformation to its austenitic phase), thereby activating the temperature-activated shape memory of the stent such that the cells 30 become biased to assume their stretched state. Thus, the sheath may constrain the stent from at least partially expanding because of the desire of the cells 30 to open to their stretched state.

Once the stent is properly positioned at the treatment location, the sheath may be retracted, exposing the stent within the body lumen, and allowing the stent to at least partially expand radially as the cells 30 assume their stretched state and/or the coiled-sheet unrolls. Preferably, the stent is self-expanding such that it expands automatically to substantially engage and open the body lumen at the treatment location. In the expanded state, the longitudinal connectors 34 of the stent 10 are preferably biased to extend axially substantially parallel to the longitudinal axis of the stent 10, as explained above.

The catheter-sheath assembly may then be withdrawn. Alternatively, an underlying balloon or other expandable member may be used to expand the stent, or a balloon catheter (not shown) may be introduced into the interior of a partially expanded stent to expand it to its enlarged position. The balloon may be inflated, thereby further radially expanding the stent, and once a desired enlarged condition is achieved, the balloon may be deflated and withdrawn.

In the enlarged condition, the protrusions 24 on the inner longitudinal edge 20 preferably engage a set of openings defined by the cells 30, thereby substantially locking the stent 10 in its enlarged condition. Thus, the protrusions 24 may allow the stent 10 to be ratcheted to a number of enlarged conditions, as long as the inner and outer longitudinal sections 40, 42 overlap and allow the protrusions 24 to engage corresponding openings defined by the cells 30, as will be appreciated by those skilled in the art.

In alternative embodiments, the stent may include outwardly-oriented hooks or barbs (not shown) for enhancing anchoring of the stent within a body passage. Pro-thrombotic material (not shown) may be provided on the exterior surfaces of the stent to enhance sealing against the wall of the body passage.

The reduced thickness region 38 in each of the connectors 34 is an important feature of the present invention. The reduced thickness regions 38 substantially change the radial strength of the stent, allowing the connectors 34 to act as hinges that may facilitate advancement of the stent through tortuous anatomy. Each connector and/or cylindrical band may act substantially independently and bend at the reduced thickness region(s) to enhance the ability of the stent to bend transverse to its longitudinal axis. Because of the resilient nature of the stent material, however, the connectors 34 may be temporarily bent during advancement through the vasculature, but may resiliently return to their substantially straight configuration once deployed within a treatment location.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalent's and alternatives falling within the spirit and scope of the appended claims.

What is claimed is:

1. A method for fabricating a stent, comprising:
providing a flat sheet of shape memory material including a length, width, and a thickness to; forming a plurality of openings in the sheet to define a multi-cellular structure;
forming a plurality of slots in the sheet aligned substantially perpendicular to the length of the sheet, the slots having a reduced thickness $t_1$ that is less than the thickness $t_0$, the slots enhancing a bending characteristic of regions of the tubular body comprising the slots, the shape memory material preventing substantially permanent deformation of the regions comprising the slots;
rolling the sheet about its length into a tubular body having a diameter configured for introduction into body lumen;
wherein the step of forming a plurality of openings in the sheet comprises forming a plurality of cells and longitudinal connectors in the sheet, longitudinally adjacent cells being connected to one another by longitudinal connectors aligned in sets substantially perpendicular to the length of the sheet, the longitudinal connectors assuming a substantially straight configuration when the tubular body is in its expanded condition.

2. The method of claim 1, wherein the plurality of slots are formed by cutting into the sheet with a saw.

3. The method of claim 1, wherein the thickness $t_1$ of the slots is not more than about two thirds the thickness $t_0$.

4. The method of claim 1, wherein the sheet comprises a shape memory alloy and wherein the plurality of slots are formed in the sheet without substantially changing mechanical properties of the shape memory alloy.

5. The method of claim 1, wherein:

the step of forming a plurality of slots comprises forming slots that intersect each set of longitudinal connectors, thereby providing a reduced thickness region in each longitudinal connector.

\* \* \* \* \*